(12) United States Patent
Jedzinski

(10) Patent No.: US 6,800,252 B1
(45) Date of Patent: Oct. 5, 2004

(54) BURSTABLE SCENT BEADS

(76) Inventor: Paul F. Jedzinski, 6 Lawrence Road Hampton, London Middlesex TW12 2RJ (GB)

( * ) Notice: Subject to any disclaimer, the term of this patent is extended or adjusted under 35 U.S.C. 154(b) by 290 days.

(21) Appl. No.: 10/071,407

(22) Filed: Feb. 7, 2002

Related U.S. Application Data

(63) Continuation-in-part of application No. 09/519,763, filed on Mar. 6, 2000.

(51) Int. Cl.$^7$ ................................................ A62B 7/08
(52) U.S. Cl. ........................ 422/123; 422/5; 422/305; 422/306; 424/76.1; 424/76.4; 424/489
(58) Field of Search .......................... 422/123, 5, 305, 422/306; 424/489, 76.1, 76.4

(56) References Cited

U.S. PATENT DOCUMENTS

| | | | |
|---|---|---|---|
| 1,958,841 A | 5/1934 | Bateholts | |
| 2,263,340 A | 11/1941 | Kraemer | |
| 2,990,640 A | 7/1961 | Burnbaum | |
| 3,041,289 A | 6/1962 | Katchen et al. | |
| 3,270,525 A | 9/1966 | Sellers | |
| 3,485,349 A | 12/1969 | Chaney, Jr, | |
| 3,640,629 A | * 2/1972 | Geiser ........................ | 401/132 |
| 4,159,631 A | 7/1979 | Lee | |
| 4,161,284 A | 7/1979 | Rattan | |
| 4,163,065 A | 7/1979 | Cilek | |
| 4,345,716 A | 8/1982 | Armstrong et al. | |
| 4,417,656 A | 11/1983 | Kato | |
| 4,927,064 A | 5/1990 | Burgin | |
| 4,950,542 A | 8/1990 | Barker | |
| 5,018,250 A | 5/1991 | Schroder | |
| 5,097,376 A | * 3/1992 | Khan ......................... | 242/341 |
| 5,303,496 A | 4/1994 | Kowalkowski | |
| 5,470,625 A | 11/1995 | Perrault | |
| 5,734,590 A | * 3/1998 | Tebbe ......................... | 700/94 |
| 5,794,459 A | 8/1998 | Ignatowski | |
| 5,972,290 A | * 10/1999 | De Sousa ..................... | 422/5 |
| 6,199,311 B1 | 3/2001 | Foster | |
| 6,315,480 B1 | 11/2001 | Martel et al. | |
| 6,375,983 B1 | * 4/2002 | Kantor et al. ............... | 424/489 |

FOREIGN PATENT DOCUMENTS

EP        0313215        4/1989

* cited by examiner

Primary Examiner—Krisanne Jastrzab

(57) ABSTRACT

A burstable bead system including a support having a surface, and a plurality of beads mounted on the surface of the support, with each of the beads comprising an outer wall defining an interior space. The outer wall of each of the beads is flexibly deformable by pressure applied to the outer wall, and is ruptureable by pressure applied to the outer wall to create an opening in the outer wall into the interior space of the bead. A scent vapor is located in the interior space of the bead such that application of pressure to the outer wall of the bead on the surface of the support releases the scent vapor from the interior space of the bead and into an environment exterior to the bead.

18 Claims, 10 Drawing Sheets

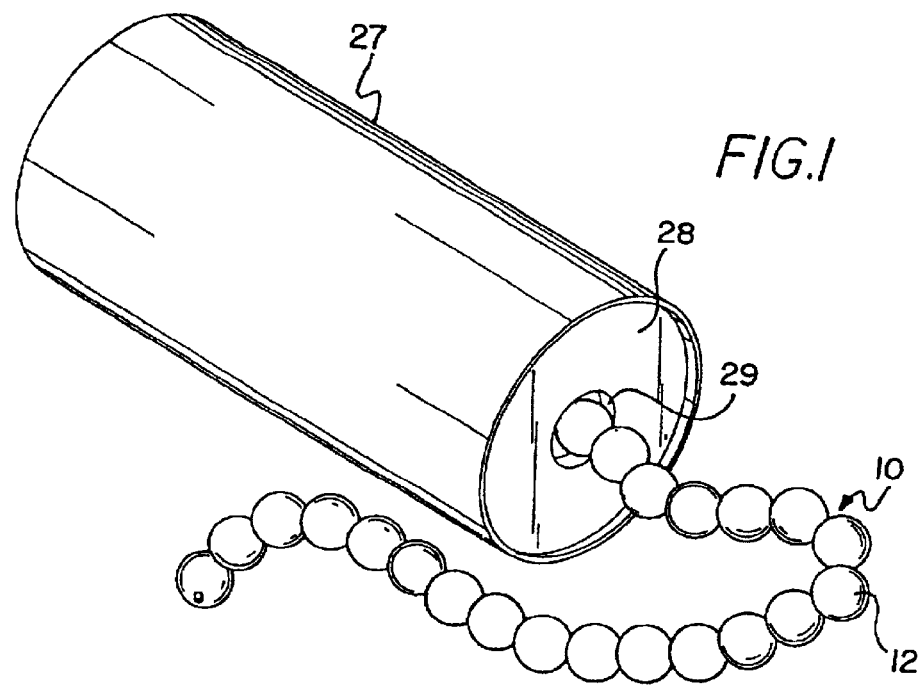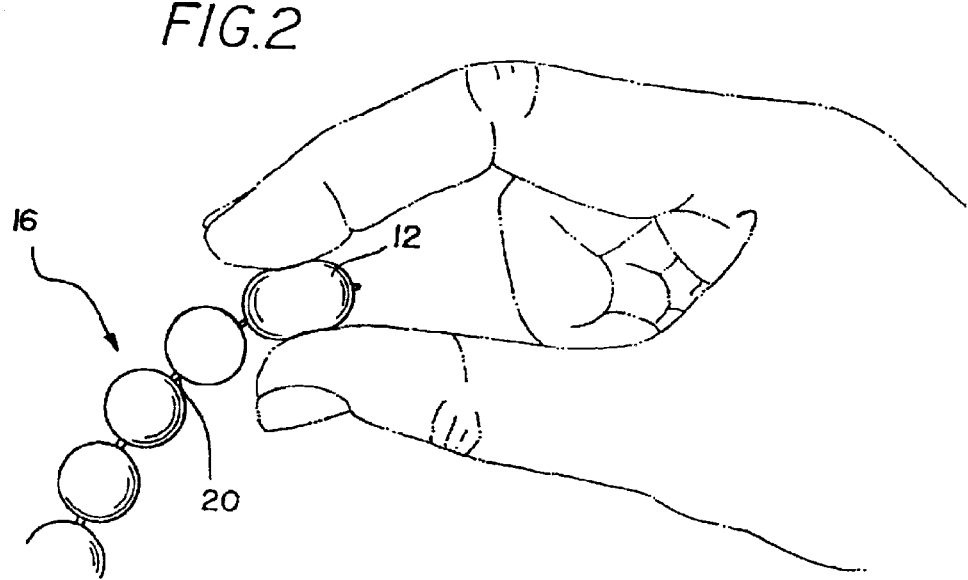

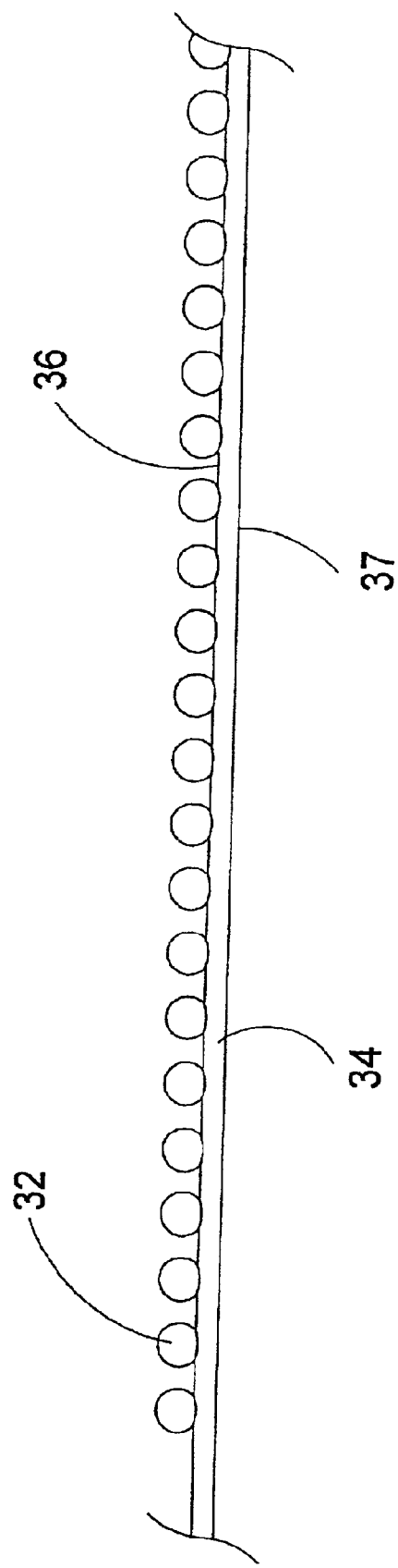

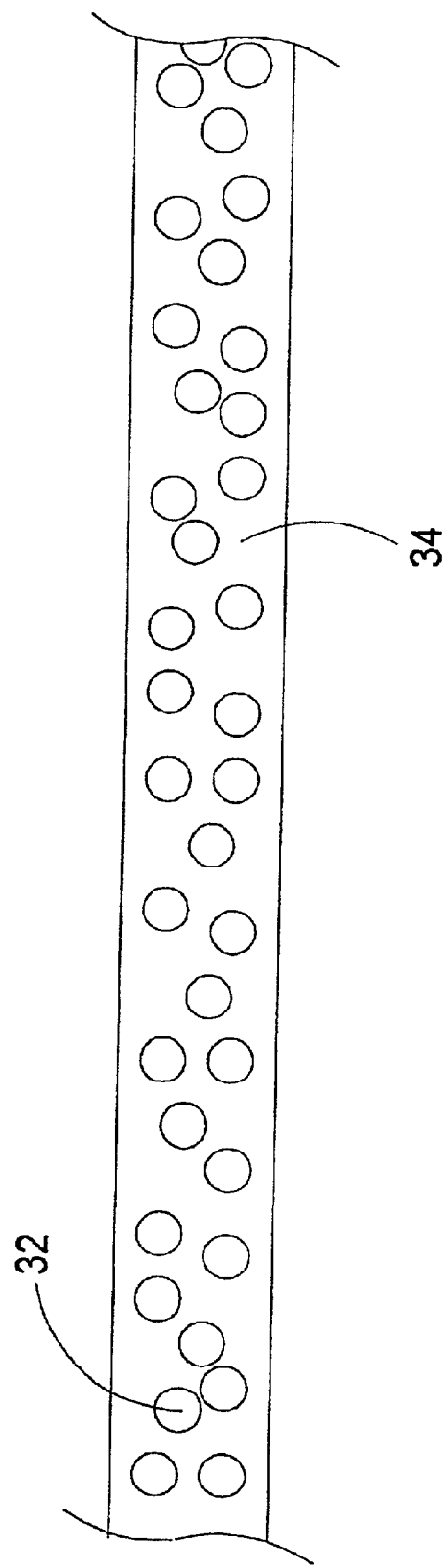

BURSTABLE SCENT BEADS

CROSS REFERENCE TO RELATED APPLICATION

This application is a continuation-in-part of U.S. patent application Ser. No. 09/519,763, filed Mar. 6, 2000.

BACKGROUND OF THE INVENTION

1. Field of the Invention

The present invention relates to scent dispersal systems and more particularly pertains to a new burstable scent bead system for permitting selective bursting of beads to release an aromatic scent from the interior of the beads.

2. Description of the Prior Art

The use of scent dispersal system is known in the prior art. More specifically, scent dispersal system heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,163,065; 5,341,634; U.S. Pat. No. Des. 358,562; U.S. Pat. Nos. 3,041,289; 1,397,458; and 4,250,997.

While these devices fulfill their respective, particular objectives and requirements, the aforementioned patents do not disclose the new burstable scent bead system of the invention as the burstable scent bead system according to the present invention substantially departs from the conventional concepts and designs of the prior art, and in so doing provides an apparatus primarily developed for the purpose of permitting selective bursting of beads to release an aromatic scent from the interior of the beads.

SUMMARY OF THE INVENTION

The present invention provides a new burstable scent beads apparatus wherein the same can be utilized for relaxation by selective bursting of beads to release an aromatic scent from the interior of the beads.

To attain this, the present invention generally comprises a support having a surface, and a plurality of beads mounted on the surface of the support, with each of the beads comprising an outer wall defining an interior space. The outer wall of each of the beads is flexibly deformable by pressure applied to the outer wall, and is ruptureable by pressure applied to the outer wall to create an opening in the outer wall into the interior space of the bead. A scent vapor is located in the interior space of the bead such that application of pressure to the outer wall of the bead on the surface of the support releases the scent vapor from the interior space of the bead and into an environment exterior to the bead.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic perspective view of a new burstable scent beads according to the present invention and a housing for the burstable scent beads.

FIG. 2 is a schematic side view of the present invention in use with a bead being crushed by a user.

FIG. 5A is a schematic side edge view of the present invention showing a plurality of the beads mounted on one side of the tape.

FIG. 6A is a schematic side view of the present invention showing a plurality of the beads mounted at various locations on a side of the length of tape.

DESCRIPTION OF THE PREFERRED EMBODIMENT

Figure 3:
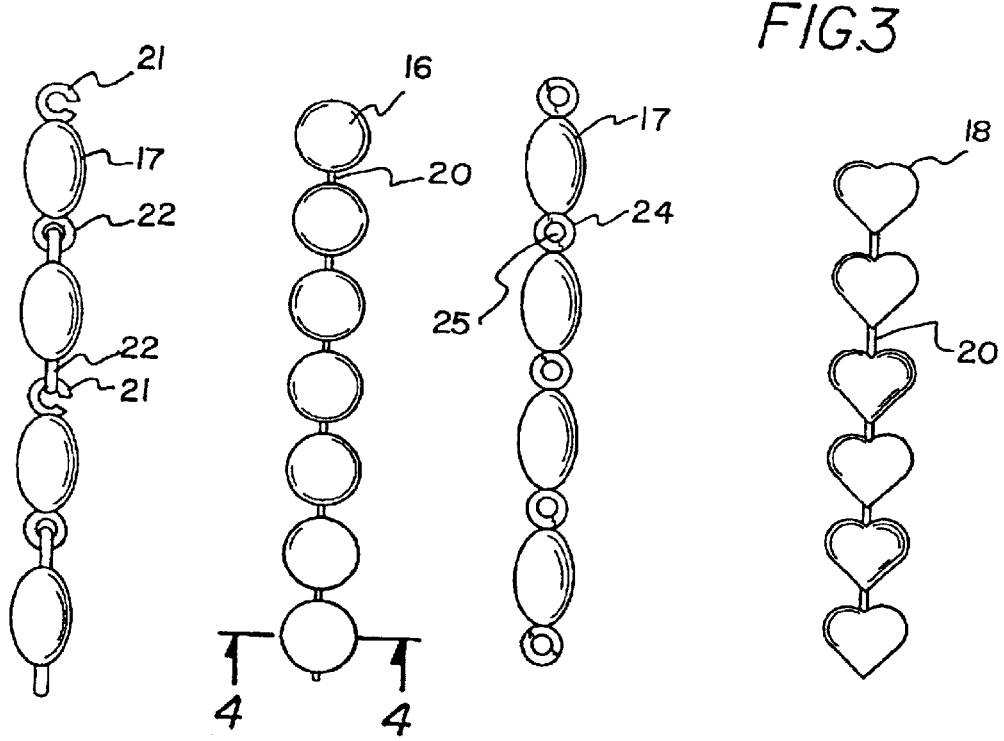
FIG. 3 is a schematic side view of the present invention illustrating various shapes the outer walls of the beads may be formed into.

With reference now to the drawings, and in particular to FIGS. 1 through 8 thereof, a new burstable scent bead system embodying the principles and concepts of the present invention and generally designated by the reference numeral 10 will be described.

One aspect of the invention, best illustrated in FIGS. 1 through 4, the burstable scent beads apparatus 10 generally comprises a plurality of interconnected beads 12 forming an elongate flexible string of burstable scent beads.

Each bead 12 comprises an outer wall 13 defining an interior space. The outer wall 13 is crushable to create an opening into the interior space of the bead 12. The outer wall 13 is formed from a material that permits the fingers of a user (such as between the thumb and forefinger) to crush the bead by bursting the outer wall of the bead by the increased pressure created in the interior of the bead by pinching the wall between the fingers of the user. Significantly, the most preferably materials for the other wall will produce a "pop" sound upon the rupturing of the outer wall and the escape of gas or air from the interior of the bead under pressure from the pinching of the outer wall. However, the bursting of the outer wall of the bead should not create any sharp edges that might injure the fingers of the user as the fingers pinch down on the edges of the burst wall.

A suitable material for the outer wall of the bead should be highly flexible but is only slightly stretchable in response to the increased pressure imposed by pinching fingers of the user. A highly suitable material is a plastic having these characteristics. One example of a suitable plastic is the plastic that is commonly used for forming the pockets of packaging material having a continuous panel with a plurality of the pockets formed on the panel. As illustrated in FIG. 3, the beads may be formed into a wide variety of shapes as desired including, for example, generally spherical beads 16, generally oval beads 17, and generally heart-shaped beads 18. Other shapes may include football-shaped, soccer ball-shaped, cartoon characters, building and the like. In one embodiment, each bead 12 has a maximum dimension of between 10 mm and 20 mm, which is highly suitable for fitting between the fingers of a user to pinch the bead.

Optionally, a scent is provided in the interior of each of the beads. The scent may be a gas, a vapor, or a liquid. In one embodiment, a scented fluid 14 is provided in the interior space of the bead 12. The fluid 14 has an aromatic scent. The fluid 14 is released from the interior space of the bead 12 when the outer wall 13 of the bead 12 is crushed. Optionally, an aromatic vapor may be provided in the interior space of the bead, although a fluid is most preferred for maximum aromatic effect. As a further option, the scent may be replaced with other compounds including medicine and disinfectants, or compounds believed to have aphrodisiac characteristics. Further, flavored fluids may also be used in the beads.

Figure 4:
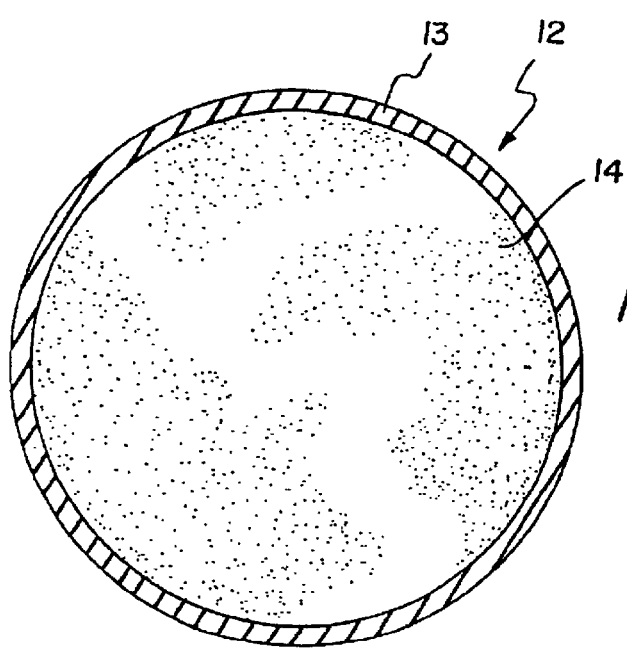
FIG. 4 is a schematic cross sectional view of the present invention taken from line 4—4 on FIG. 3.

In use, as illustrated in FIG. 2, a user places a bead 12 between their fingers and forcibly compresses the bead in a crushing fashion, and the increased pressure in the interior of the bead serves to burst the outer wall of the bead and release the scented fluid 14. Specifically, the burstable scent beads 10 comprise a plurality of interconnected beads 12 forming an elongate flexible burstable scent beads. With reference to FIG. 4, each bead 12 comprises an outer wall 13 defining an enclosed interior space. The outer wall 13 is crushable to create an opening into the interior space of the bead 12.

In a preferred embodiment, a flexible line 20 interconnects the plurality of beads together into a flexible string of burstable scent beads 10. In one embodiment of the invention, a flexible portion 24 interconnects adjacent beads together so that the beads may be separated at the flexible portion 24 by some type of separation method that destroys the ability to connect the beads, such as by tearing of the string, for example. The flexible portion 24 is preferably formed integrally with the adjacent beads. The flexible portion 24 preferably has a hole 25 therethrough for permitting threading of a line 20 therethrough to attach a bead 12 to an item such as an article of jewelry. Optionally, as shown in FIG. 3, each bead 12 may include diametrically opposed hook and loop portions 21,22. The hook portion 21 of one of the beads is insertable into the loop portion 22 of an adjacent bead 12 such that the beads are interconnected.

In an ideal embodiment, a housing 27 is provided for storing the burstable scent beads. While the housing may fashioned in any shape, in an illustrative embodiment, the housing 27 is generally cylindrical and has an interior and a pair of circular ends. As shown in FIG. 1, one of the ends 28 of the housing 27 has a hole 29 into the interior of the housing 27. The burstable scent beads are disposed in the interior of the housing 27 and are removable from the interior of the housing 27 through the hole 29 of the end 28 of the housing 27.

In another aspect of the invention, shown in FIGS. 5 through 8, a burstable bead system 30 is provided that includes a support having a surface, and a plurality of beads 32 that are mounted on the surface of the support. Each of the beads 32 may comprise an outer wall defining an interior space, and the outer wall of each of the beads being flexibly deformable by pressure applied to the outer wall. The outer wall of each of the beads may also be ruptureable by pressure applied to the outer wall to create an opening in the outer wall into the interior space of the bead.

A scent vapor may be located in the interior space of the bead 32 such that application of pressure to the outer wall of the bead on the surface of the support releases the scent vapor from the interior space of the bead and into an environment exterior to the bead.

In one embodiment of the system 30, the support comprises a length of flexible tape 34 with opposite sides 36, 37, and the plurality of beads are mounted on a first one 36 of the opposite sides of the length of tape (see FIG. 5A). Optionally, in another embodiment of the invention, a plurality of the beads is mounted on a second one 37 of the opposite sides of the length of tape 34 such that beads are located on each of the opposite sides 36, 37 of the length of tape (see FIG. 5D).

Optionally, the length of tape 34 may have a metalized coating for magnetically recording signals representing video images and/or signals representing audible sounds.

Figure 5B:
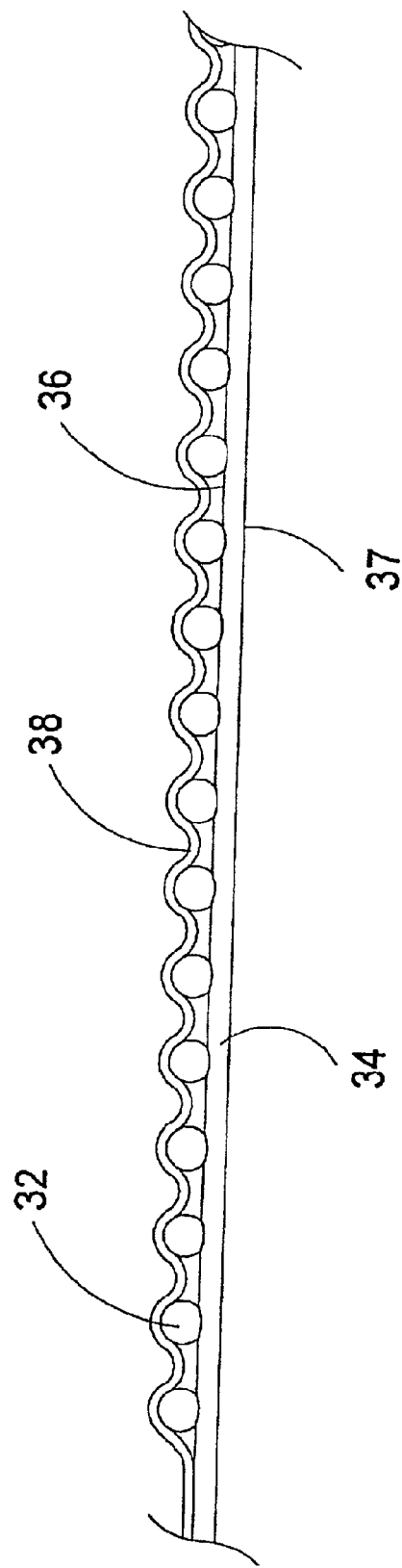
FIG. 5B is a schematic side edge view of the present invention showing a plurality of the beads mounted between two lengths of tape.
Figure 5C:
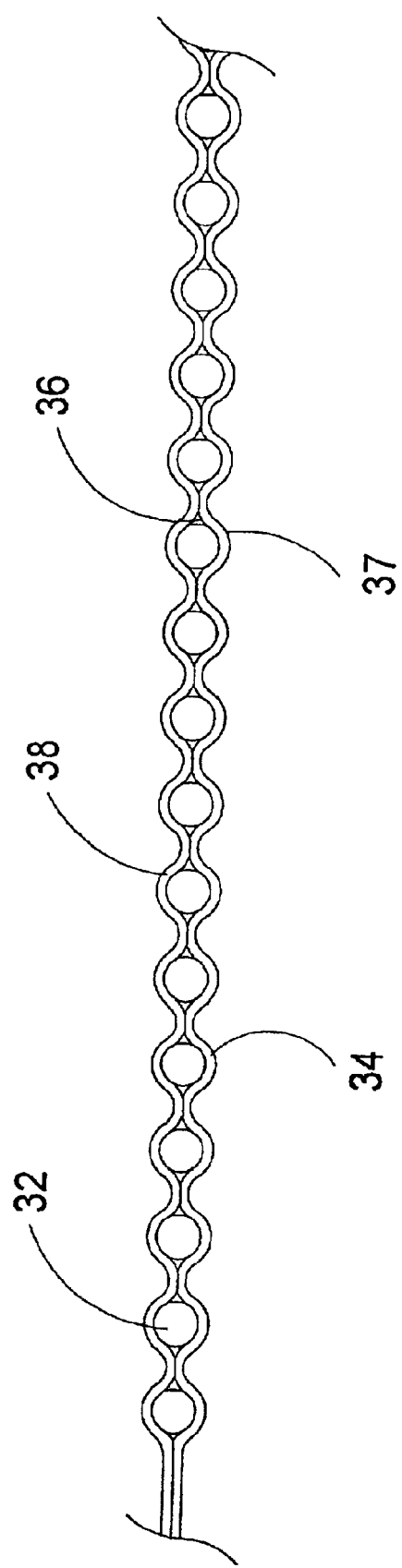
FIG. 5C is a schematic side edge view of the present invention showing a plurality of the beads mounted between two lengths of tape in a second configuration.
Figure 5D:
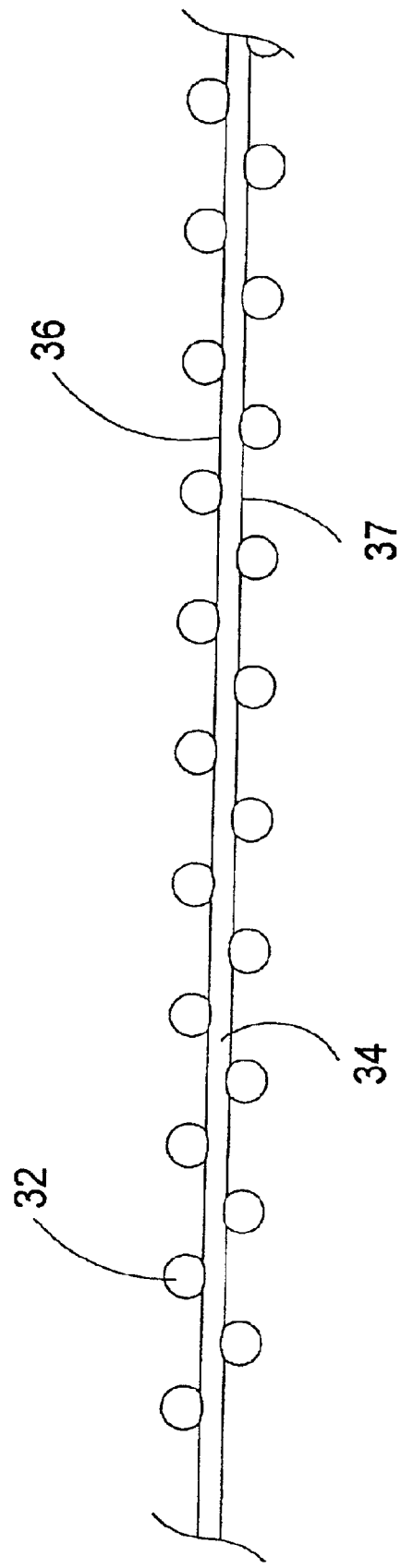
FIG. 5D is a schematic side edge view of the present invention showing a plurality of the beads mounted on opposite sides of the length of tape.

As a further option, the length of tape 34 may comprise a first length of tape, and a second length of tape 38 may be provided with the second length of tape being positioned adjacent to the first side 36 of the first length of tape 34 with the plurality of beads 32 being located between the first 34 and second 38 lengths of tape (see FIGS. 5B and 5C). Optionally, one or both of the lengths 34, 38 of tape may be relatively straight, or one or both of the lengths may be conformed to the exterior of the beads.

Figure 6B:
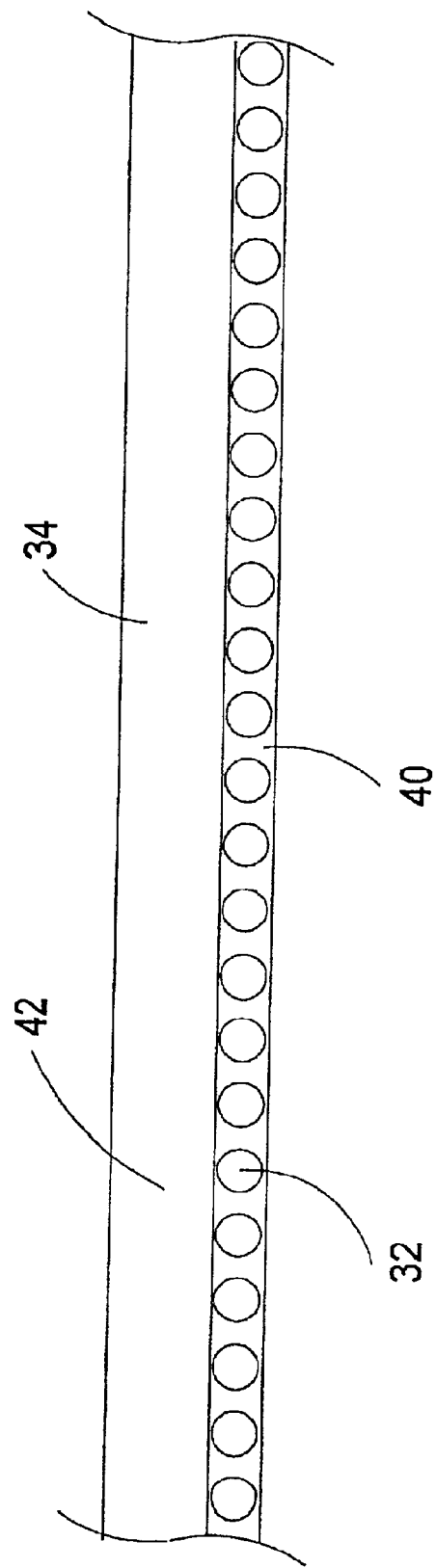
FIG. 6B is a schematic side view of the present invention showing a plurality of the beads mounted in a longitudinal band extending along a lengthwise direction of the length of tape.

The plurality of beads 32 may be located in a longitudinal band 40 extending in a longitudinal direction of the length of tape (see FIG. 6B). Optionally, signals may be recorded on the length of tape on another longitudinal band 42 located adjacent to the longitudinal band of the beads.

Figure 7:
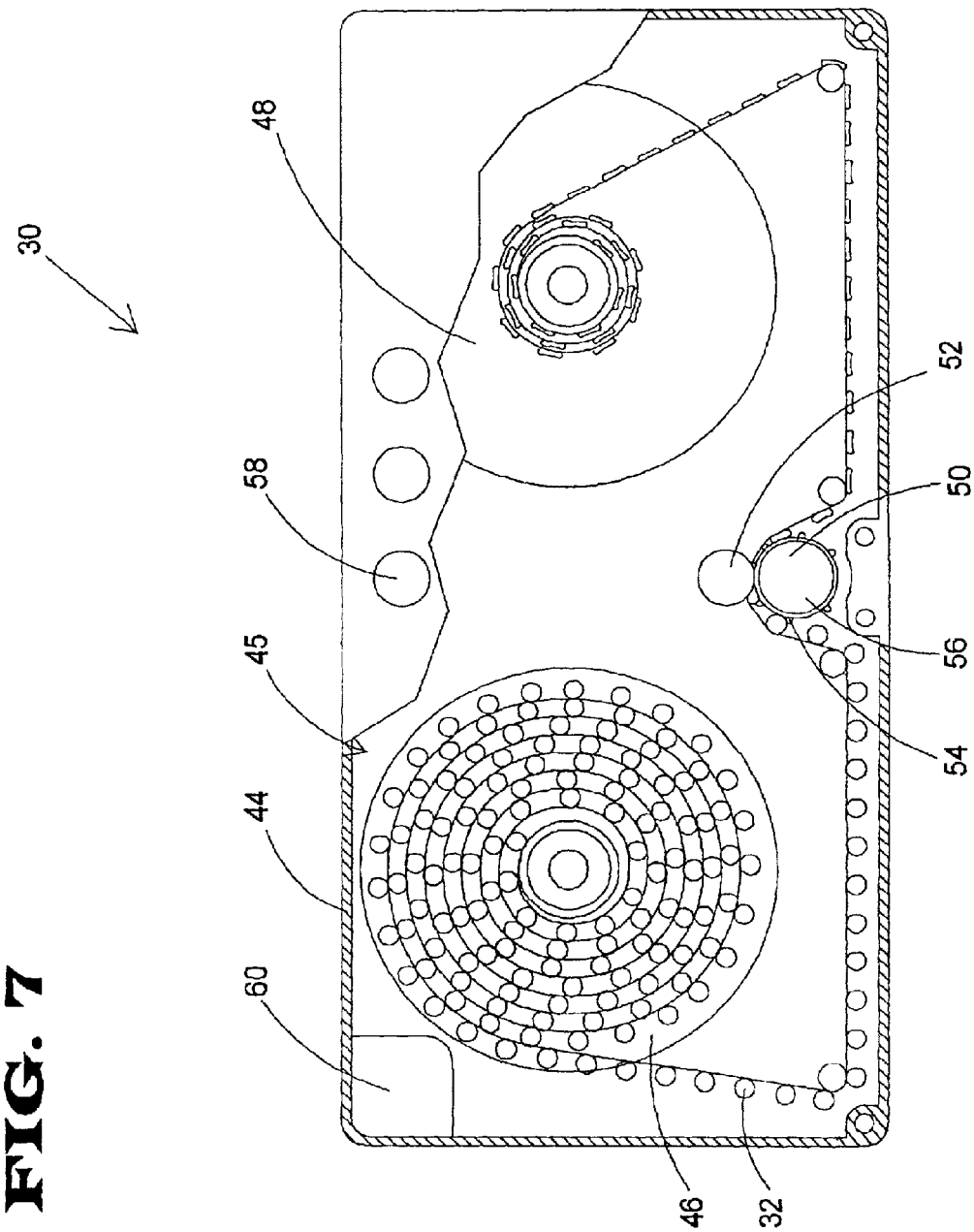
FIG. 7 is a schematic sectional view of a housing of the present invention showing the length of tape positioned therein.

The system may include a housing 44 having an interior 45 with the length of tape 34 being located in the interior (see FIG. 7). The housing 44 may have a pair of spools 46, 48 located in the interior 46 of the housing. A first one 46 of the spools may comprise a supply spool and a second one 48 of the spools may comprise a take-up spool. A portion of the length of tape may be wound about the supply spool 46 and a portion of the length of tape being wound about the take-up spool 48 such that a portion of the length of tape extends between the spools. A pair of rollers 50, 52 may be positioned in the interior 46 of the housing 44, and may be positioned in the housing such that outer circumferential surfaces of the rollers are in contact with each other and may be rotated with each other. A portion of the length of tape 34 extending between the spools passes between the rollers 50, 52 such that the rollers exert pressure against the beads on the tape for bursting the beads on the tape. Optionally, the outer circumferential surface of one of the rollers has a plurality of protrusions 54 formed thereon for puncturing the outer walls of the beards. A motor 56 may be provided for rotating at least one of the rollers, and controls may be provided for controlling operation of the motor. The controls may include a switch 58 for selectively supplying power to the motor. A battery 60 may also be provided for supplying electrical power to the motor.

In one embodiment of the invention, the housing is configured to be insertable into a VHS video tape player, and the rollers may be rotated by the mechanism causing the spools to rotate.

Figure 8:
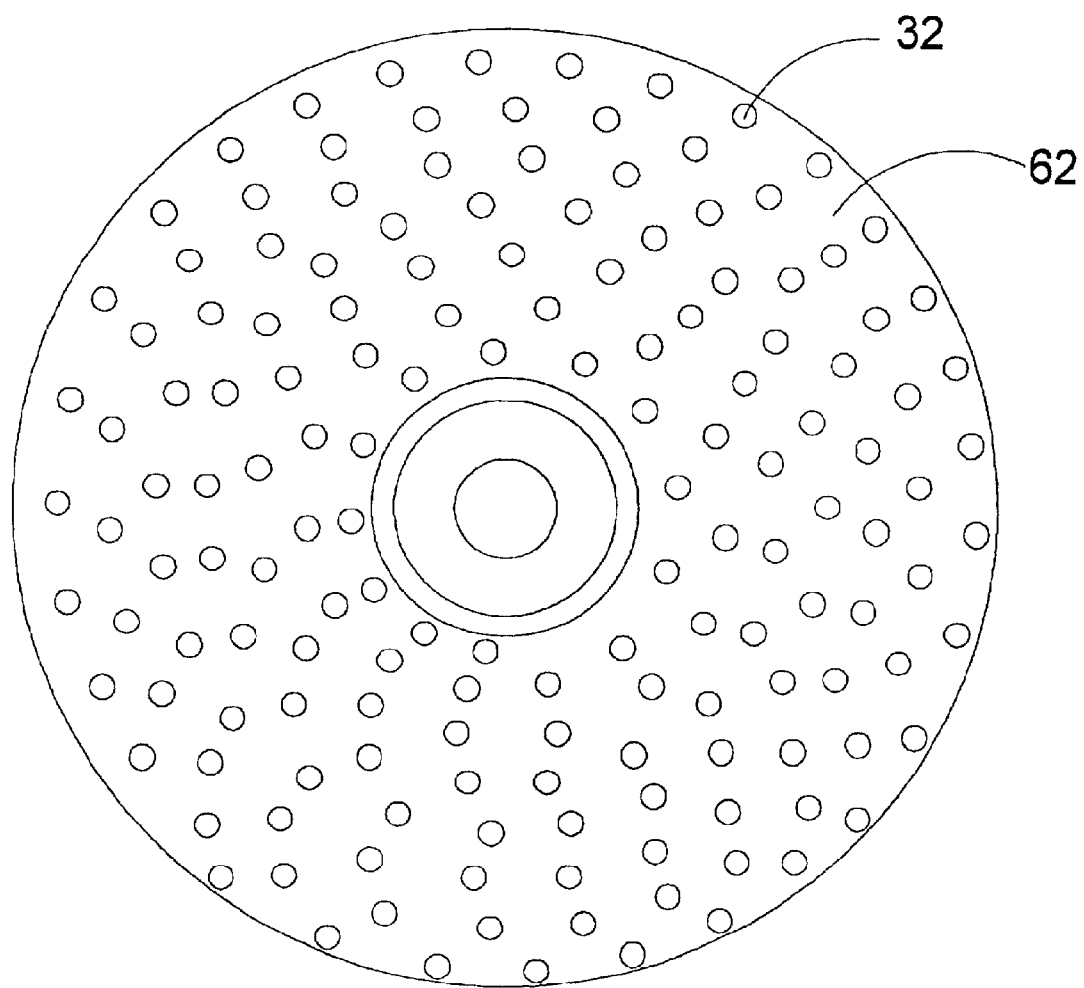
FIG. 8 is a schematic top view of a disc of the present invention having the plurality of beads mounted on one side thereof.

In another embodiment of the invention, the support comprises a disc 62 with opposite sides, with one of the opposite sides comprising the surface, and the plurality of beads being mounted on one of the opposite sides (see FIG. 8).

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A burstable bead system comprising:
   a support having a surface; and
   a plurality of beads mounted on the surface of the support, each of the beads comprising an outer wall defining an interior space, the outer wall of each of the beads being flexibly deformable by pressure applied to the outer wall, the outer wall of each of the beads being ruptureable by pressure applied to the outer wall to create an opening in the outer wall into the interior space of the bead; and
   a scent vapor being located in the interior space of the bead such that application of pressure to the outer wall of the bead on the surface of the support releases the scent vapor from the interior space of the bead and into an environment exterior to the bead.

2. The system of claim 1 wherein the support comprises a length of flexible tape with opposite sides, the plurality of beads being mounted on a first one of the opposite sides of the length of tape.

3. The system of claim 2 wherein a plurality of the beads is mounted on a second one of the opposite sides of the length of tape such that beads are located on each of the opposite sides of the length of tape.

4. The system of claim 2 wherein the length of tape has a metalized coating for magnetically recording signals representing video images thereon.

5. The system of claim 2 wherein the length of tape has a metalized coating for magnetically recording signals representing audible sounds thereon.

6. The system of claim 2 wherein the length of tape comprises a first length of tape, and additionally comprising a second length of tape, the second length of tape being positioned adjacent to the first side of the first length of tape with the plurality of beads being positioned between the first and second lengths of tape.

7. The system of claim 2 wherein the plurality of beads are located in a longitudinal band extending in a longitudinal direction of the length of tape.

8. The system of claim 7 wherein signals are recorded the length of tape on another longitudinal band located adjacent to the longitudinal band of the beads.

9. The system of claim 2 additionally comprising a housing having an interior with the length of tape being located in the interior, the housing having a pair of spools located in the interior of the housing, a first one of the spools comprising a supply spool and a second one of the spools comprising a take-up spool, a portion of the length of tape being wound about the supply spool and a portion of the length of tape being wound about the take-up spool such that a portion of the length of tape extends between the spools.

10. The system of claim 9 wherein a pair of rollers are positioned in the interior of the housing, the pair of rollers being positioned such that outer circumferential surfaces of the rollers are in contact with each other and are rotatable against each other, and wherein a portion of the length of tape extending between the spools passes between the rollers such that the rollers exert pressure against the beads on the tape for bursting the beads on the tape.

11. The system of claim 10 wherein the outer circumferential surface of one of the rollers has a plurality of protrusions formed thereon for puncturing the outer walls of the beards.

12. The system of claim 10 additionally comprising a motor for rotating at least one of the rollers.

13. The system of claim 12 additionally comprising control means for controlling operation of the motor.

14. The system of claim 12 wherein the control means comprises a switch for selectively supplying power to the motor.

15. The system of claim 12 additionally comprising a battery for supplying electrical power to the motor.

16. The system of claim 9 wherein the housing is configured to be insertable into a VHS video tape player.

17. The system of claim 1 wherein the support comprises a disc with opposite sides, one of the opposite sides comprising the surface, the plurality of beads being mounted on one of the opposite sides.

18. The system of claim 1 wherein the support comprises a length of flexible tape with opposite sides, the plurality of beads being mounted on a first one of the opposite sides of the length of tape;
   wherein the plurality of beads are located in a longitudinal band extending in a longitudinal direction of the length of tape;
   a housing having an interior with the length of tape being located in the interior, the housing having a pair of spools located in the interior of the housing, a first one of the spools comprising a supply spool and a second one of the spools comprising a take-up spool, a portion of the length of tape being wound about the supply spool and a portion of the length of tape being wound about the take-up spool such that a portion of the length of tape extends between the spools;

a pair of rollers being positioned in the interior of the housing, the pair of rollers being positioned such that outer circumferential surfaces of the rollers are in contact with each other and are rotatable against each other, and wherein a portion of the length of tape extending between the spools passes between the rollers such that the rollers exert pressure against the beads on the tape for bursting the beads on the tape;

wherein the outer circumferential surface of one of the rollers has a plurality of protrusions formed thereon for puncturing the outer walls of the beards;

a motor for rotating at least one of the rollers; and control means for controlling operation of the motor.

* * * * *